US011565035B2

(12) United States Patent
Volkar et al.

(10) Patent No.: US 11,565,035 B2
(45) Date of Patent: Jan. 31, 2023

(54) SYSTEMS AND METHODS FOR SPLIT BOLUS PROTOCOL GENERATION (71) Applicant: BAYER HEALTHCARE LLC, Whippany, NJ (US)

(72) Inventors: John Volkar, Valencia, PA (US); Corey Kemper, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 664 days.

(21) Appl. No.: 16/619,515

(22) PCT Filed: Jun. 14, 2018

(86) PCT No.: PCT/US2018/037492
§ 371 (c)(1),
(2) Date: Dec. 5, 2019

(87) PCT Pub. No.: WO2018/232085
PCT Pub. Date: Dec. 20, 2018

(65) Prior Publication Data
US 2020/0197599 A1 Jun. 25, 2020

Related U.S. Application Data (60) Provisional application No. 62/520,728, filed on Jun. 16, 2017.

(51) Int. Cl.
*A61B 6/00* (2006.01)
*A61M 5/00* (2006.01)
(Continued)

(52) U.S. Cl.
CPC ............. *A61M 5/007* (2013.01); *A61B 6/465* (2013.01); *A61B 6/481* (2013.01); *A61B 6/54* (2013.01);
(Continued)

(58) Field of Classification Search
CPC .......... A61M 5/007; A61M 2205/3389; A61M 2205/50; A61M 2205/52;
(Continued)

(56) References Cited

U.S. PATENT DOCUMENTS 5,583,902 A 12/1996 Bae
5,840,026 A 11/1998 Uber, III et al.
(Continued)

FOREIGN PATENT DOCUMENTS

JP 4417621 B2 2/2010
JP 5203971 B2 6/2013
(Continued)

OTHER PUBLICATIONS

Brook Olga R.; et al., "Split-Bolus Spectral Multidedector CT of the Pancreas: Assessment of Radiation Dose and Tumor Conspicuity", Radiology, Oct. 2013, vol. 269 / No. 1, 139-148.
(Continued)

*Primary Examiner* — Don K Wong
(74) *Attorney, Agent, or Firm* — James R. Stevenson; Bryan P. Clark (57) ABSTRACT Described is an injector system for implementing a split bolus injection procedure. The injector system includes a processor and a non-transitory storage medium having programming instructions stored therein that, when executed by the processor, enable the injector system to operate as a parameter generation system for use in determining parameters associated with a split bolus injection protocol via which injection of the contrast agent by the injector system is controlled. The split bolus injection protocol includes at least a loading injection and a diagnostic injection, wherein the loading injection is performed before the diagnostic injection, and wherein a pause separates the loading injection from the diagnostic injection. Also described is a
(Continued)

method for patient imaging using a split bolus injection technique and a system having an imaging device and the injector system described above.

20 Claims, 5 Drawing Sheets

(51) Int. Cl.
    *G16H 20/17*     (2018.01)
    *G16H 10/60*     (2018.01)
    *G16H 15/00*     (2018.01)
    *G16H 70/40*     (2018.01)
    *G16H 40/63*     (2018.01)
    *G16H 70/20*     (2018.01)

(52) U.S. Cl.
    CPC .............. *G16H 10/60* (2018.01); *G16H 15/00* (2018.01); *G16H 20/17* (2018.01); *G16H 40/63* (2018.01); *G16H 70/20* (2018.01); *G16H 70/40* (2018.01); *A61M 2205/3303* (2013.01); *A61M 2205/3334* (2013.01); *A61M 2205/3389* (2013.01); *A61M 2205/50* (2013.01); *A61M 2205/502* (2013.01); *A61M 2205/52* (2013.01)

(58) Field of Classification Search
    CPC .... A61M 2205/502; A61M 2205/3303; A61M 2205/3334; G16H 20/17; G16H 70/40; G16H 70/20; G16H 15/00; G16H 10/60; G16H 40/63; A61K 49/0438; A61B 6/032; A61B 6/481; A61B 6/504; A61B 6/545; G06T 2207/10081; G06T 2207/30101; G06T 11/006; G06T 7/0012; G06T 7/0081; G06T 2207/20104; G06T 2211/404
    See application file for complete search history.

(56) References Cited

U.S. PATENT DOCUMENTS

| | | | |
|---|---|---|---|
| 6,385,483 B1 | 5/2002 | Uber, III et al. | |
| 7,553,294 B2 | 6/2009 | Lazzaro et al. | |
| 7,925,330 B2 | 4/2011 | Kalafut et al. | |
| 8,295,914 B2 | 10/2012 | Kalafut et al. | |
| 8,428,694 B2 | 4/2013 | Kalafut et al. | |
| 8,699,770 B2 | 4/2014 | Kemper et al. | |
| 9,008,759 B2 | 4/2015 | Kalafut et al. | |
| 9,302,044 B2 | 4/2016 | Kalafut et al. | |
| 9,421,330 B2 | 8/2016 | Kalafut et al. | |
| 9,456,798 B2 * | 10/2016 | Xue ...................... | A61B 6/486 |
| 9,750,953 B2 | 9/2017 | Kalafut | |
| 9,949,704 B2 | 4/2018 | Kalafut et al. | |
| 9,959,389 B2 | 5/2018 | Kalafut | |
| 2010/0030073 A1 | 2/2010 | Kalafut et al. | |
| 2013/0109966 A1 | 5/2013 | Assmann et al. | |
| 2017/0258982 A1 | 9/2017 | Kemper | |

FOREIGN PATENT DOCUMENTS

| | | |
|---|---|---|
| RU | 2556619 C1 | 7/2015 |
| WO | 2006055813 A2 | 5/2006 |
| WO | 2006058280 A2 | 6/2006 |
| WO | 2008085421 A2 | 7/2008 |
| WO | 2009012023 A1 | 1/2009 |
| WO | 2013172811 A1 | 11/2013 |

OTHER PUBLICATIONS

Chen C.; et al., "Diagnostic Performance of Split-Bolus Portal Venous Phase Dual-Energy CT Urography in Patients With Hematuria", AJR, May 2016, vol. 206 / No. 5, 1013-1022.
Choe Yeon Hyeon; et al., "Biphasic and Discontinuous Injection of Contrast Material for Thin-Section Helical CT Angiography of the Whole Aorta and Iliac Arteries", AJR, Feb. 2001, vol. 176 / No. 2, 454-456.
Chow Lawrence C.; et al., "Split-Bolus MDCT Urography with Synchronous Nephrographic and Excretory Phase Enhancement", AJR, Aug. 2007, vol. 189 / No. 2, 314-322.
"International Report on Patentability from PCT Application No. PCT/US2018/037492", Dec. 26, 2019.
Karlo Christoph A.; et al., "Split-bolus dual-energy CT urography: protocol optimization and diagnostic performance for the detection of urinary stones", Abdominal Imaging, Mar. 17, 2013, 38, 1136-1143.
Kekelidze Maka; et. al., "Kidney and Urinary Tract Imaging: Triple-Bolus Multidetector CT Urography as a One-Stop Shop—Protocol Design, Opacification, and Image Quality Analysis", Radiology, May 2010, vol. 255 / No. 2, 508-516.
Kerl J. Matthias; et al., "Right Heart: Split-Bolus Injection of Diluted Contrast Medium for Visualization at Coronary CT Angiography", Radiology, May 2008, vol. 247 / No. 2, 356-364.
Leung V.; et al., "Implementation of a split-bolus single-pass CT protocol at a UK major trauma centre to reduce excess radiation dose in trauma pan-CT", Clinical Radiology, 2015, 70, 1110-1115.
Leung V.J.; et al., "Early Experience with a split-bolus single-pass CT protocol in paediatric trauma", Clinical Radiology, 2017, 72, 497-501.
Scialpi Michele; et al., "FDG PET and Split-Bolus Multi-Detector Row CT Fusion Imaging in Oncologic Patients: Preliminary Results", Radiology, Mar. 2016, vol. 278/Issue 3, 873-880.
Scialpi Michele; et al., "Split-Bolus Single-Pass Multidetector-Row CT Protocol for Diagnosis of Acute Pulmonary Embolism", Iran J. Radiol., Jan. 14, 2016, vol. 13 / No. 1, 1-7.
Sung Mi Kim; et al., "Current status of low dose multi-detector CT in the urinary tract", World Journal of Radiology, Nov. 28, 2011, vol. 3, Issue 11, 256-265.
Yeo Yu Jin; et al., "Diagnostic Efficiency of Split-Bolus Dual-Energy Computed Tomography for Patients With Suspected Urinary Stones", J. Comput Assist. Tomogr., Jan./Feb. 2015, vol. 39 / No. 1, 25-31.

* cited by examiner

Patient

| | | |
|---|---|---|
| Weight | 55 | kg |
| Height | 150 | cm |
| Age | 60 | yr |

○ Male   ● Female

[Select Compartments]

Injection Protocol

Concentration  300  mg/ml

| | | Rate | Volume | Duration |
|---|---|---|---|---|
| ☑ | Contrast | 4 | 100 | 25 |
| ☑ | Saline | 4 | 40 | 10 |
| ☑ | Pause | | | 35 |
| ☑ | Contrast | 4 | 40 | 10 |
| ☑ | Saline | 4 | 40 | 10 |
| ☐ | | | | |

Total simulation time (seconds)  250

Tube Voltage

[80kVp]  [100kVp]  [120kVp]  [140kVp]

Scan Timings

| | Delay | Duration |
|---|---|---|
| ▓ Scan 1 | 100 sec | 10 sec |
| ☐ Scan 2 | | |
| ☐ Scan 3 | | |
| ☐ Scan 4 | | |

[Compute Delay Timing]

SYSTEMS AND METHODS FOR SPLIT BOLUS PROTOCOL GENERATION

CROSS REFERENCE TO RELATED APPLICATION

This application is a 371 national phase application of International Patent Application No. PCT/US2018/037492, filed Jun. 14, 2018, and claims priority to U.S. Provisional Patent Application No. 62/520,728 filed on Jun. 16, 2017, the entire contents of which are hereby incorporated by reference.

BACKGROUND

Field

Embodiments of this disclosure are generally directed to systems and methods for fluid delivery, and, particularly, to systems and methods for delivery of a contrast agent to a patient using a split bolus technique.

Description of Related Art

Contrast-based medical imaging is an indispensable diagnostic tool that is widely used in hospitals and medical facilities around the world. The undesirable side effect of such imaging is exposing the patient to ionizing radiation that the patient otherwise would not have received. According to the International Atomic Energy Agency (IAEA), a chest or abdomen CT scan exposes the patient to 5 to 20 mSv as opposed to less than 0.1 mSv in an ordinary chest x-ray. Unfortunately, lowering the exposure in a scan has a detrimental effect on the quality of the acquired images, which in turn can negatively affect the diagnosis. The rise in the awareness of the harms of exposure to excessive x-ray radiation in in recent years has resulted in a great focus on the As Low As Reasonably Achievable ("ALARA") principle and has stimulated significant interest in ways to optimize medical imaging procedures in order to reduce the patient's exposure to such harmful radiation.

One known, but rarely used, technique to reduce a patient's radiation exposure is referred to as the split bolus technique. The split bolus technique is a technique that enables a single scan acquisition to be used in place of multiple acquisitions which, in turn, reduces a patient's radiation exposure. In essence, the split bolus technique replaces the single continuous injection that is common in most contrast-based medical imaging procedures with two or three separate contrast injections with a delay or pause occurring between the injections. Because each of the separate injections reach and are absorbed by different portions of the body at different times, the split bolus injection can provide simultaneous enhancement of different body portions. If the acquisition scan is correctly timed to coincide with the simultaneous enhancement period, the split bolus technique allows for a single scan to be performed to acquire information about multiple portions of the body, thus eliminating the need to perform multiple scans to acquire this information.

While generally effective in helping to reduce a patient's radiation exposure, the split bolus technique is still viewed as a niche practice, reserved generally for research studies and advanced practitioners, and not commonly applied in the clinical setting. One reason for this is believed to be the difficulty in developing and implementing split bolus injection protocols in a consistent and practical manner that can be widely employed.

SUMMARY

An object of certain embodiments of this disclosure is to provide systems and methods that can be used to implement a split bolus injection procedure. The system can include a parameter generation system that can determine the parameters of a split bolus protocol that includes multiple contrast injections.

Various aspects of the present disclosure may be further characterized by one or more of the following clauses:

Clause 1: An injector system for injecting a contrast agent into a patient in connection with a contrast enhanced imaging procedure to be performed on the patient using an imaging system, the injector system comprising: a processor; and a non-transitory storage medium having programming instructions stored therein that, when executed by the processor, enable the injector system to operate as a parameter generation system for use in determining parameters associated with a split bolus injection protocol via which injection of the contrast agent by the injector system is controlled, wherein the split bolus injection protocol includes at least a loading injection and a diagnostic injection, wherein the loading injection is performed before the diagnostic injection, and wherein a pause separates the loading injection from the diagnostic injection, and wherein the injector system is configured to perform the loading injection and the diagnostic injection according to the parameters determined by the parameter generation system.

Clause 2: The injector system of clause 1, wherein the parameter generation system determines one or more of a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

Clause 3: The injector system of clause 2, wherein the parameter generation system determines the volume of the contrast agent to be injected during the loading injection, the flow rate of the contrast agent to be injected during the loading injection, the volume of the contrast agent to be injected during the diagnostic injection, and the flow rate of the contrast agent to be injected during the diagnostic injection.

Clause 4: The injector system of any of clauses 1-3, wherein the split bolus injection protocol includes a second loading injection, and the parameter generation system determines at least one of a volume of the contrast agent to be injected during the second loading injection and a flow rate of the contrast agent to be injected during the second loading injection.

Clause 5: The injector system of clause 2, wherein the split bolus injection protocol includes a second loading injection, and the parameter generation system determines at least one of a volume of the contrast agent to be injected during the second loading injection and a flow rate of the contrast agent to be injected during the second loading injection.

Clause 6: The injector system of any of clauses 1-5, further comprising a graphical user interface configured to display the parameters determined by the parameter generation system.

Clause 7: The injector system of clause 6, wherein the graphical user interface is configured to display a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

Clause 8: The injector system of any of clauses 1-7, wherein the parameter generation system determines a volume of the contrast agent that is to be injected during the loading injection and a volume of the contrast agent that is to be injected during the diagnostic injection at least partly on the basis of a concentration of the contrast agent and at least partly on the basis of a function X having a value that differs depending upon a weight of a patient.

Clause 9: The injector system of clause 8, further comprising an input device for entering into the parameter generation system the concentration of the contrast agent and the weight of the patient.

Clause 10: The injector system of clause 8, wherein the volume of the contrast agent that is to be injected during the loading injection and the volume of the contrast agent that is to be injected during the diagnostic injection are each independently calculated using the formula: V=weight*X*Y, wherein Y is a function of the concentration of the contrast agent, and wherein X may differ between the loading injection and the diagnostic injection.

Clause 11: The injector system of clause 10 wherein X is determined for the weight of a particular patient from an algorithm in which X is calculated as a function of weight.

Clause 12: The injector system of clause 10 wherein X is determined for the weight of a particular patient from a table wherein X is set forth as a function of weight.

Clause 13: The injector system of any of clauses 1-12, wherein the injector system is configured to send a timing signal to an imaging system after the diagnostic injection.

Clause 14: A method for patient imaging using a split bolus injection technique, the method comprising: determining, by a parameter generation system, parameters of a loading injection and a diagnostic injection, wherein each of the loading injection and the diagnostic injection comprise a volume of a contrast agent; performing, by an injector system, the loading injection so as to deliver the loading injection to a patient; performing, by the injector system, the diagnostic injection so as to deliver the diagnostic injection to the patient, wherein a pause of a predetermined period of time occurs between the loading injection and the diagnostic injection;

sending, from the injector system to an imaging system, a timing signal indicating that the diagnostic injection has been completed; and performing, by the imaging system, an imaging procedure of the patient in response to receiving the timing signal.

Clause 15: The method of clause 14, wherein the parameter generation system determines one or more of a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

Clause 16: The method of clause 15, wherein the parameter generation system determines the volume of the contrast agent to be injected during the loading injection, the flow rate of the contrast agent to be injected during the loading injection, the volume of the contrast agent to be injected during the diagnostic injection, and the flow rate of the contrast agent to be injected during the diagnostic injection.

Clause 17: The method of any of clauses 14-16, further comprising:

determining, by the parameter generation system, parameters of at least one of a volume of the contrast agent to be injected during a second loading injection and a flow rate of the contrast agent to be injected during the second loading injection.

Clause 18: The method of any of clauses 14-17, further comprising:

displaying, on a graphical user interface, the parameters determined by the parameter generation system.

Clause 19: The method of clause 18, wherein the graphical user interface displays a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

Clause 20: The method of any of clauses 14-19, wherein the parameter generation system determines a volume of the contrast agent that is to be injected during the loading injection and a volume of the contrast agent that is to be injected during the diagnostic injection at least partly on the basis of a concentration of the contrast agent and at least partly on the basis of a function X having a value that differs depending upon a weight of a patient.

Clause 21: The method of clause 20, wherein the concentration of the contrast agent and the weight of the patient are input via an input device.

Clause 22: The method of clause 20, wherein the volume of the contrast agent that is to be injected during the loading injection and the volume of the contrast agent that is to be injected during the diagnostic injection are each independently calculated using the formula: V=weight*X*Y, wherein Y is a function of the concentration of the contrast agent, and wherein X may differ between the loading injection and the diagnostic injection.

Clause 23: The method of clause 22 wherein X is determined for the weight of a particular patient from an algorithm in which X is calculated as a function of weight.

Clause 24: The method of clause 22 wherein X is determined for the weight of a particular patient from a table wherein X is set forth as a function of weight.

Clause 25: A system for patient imaging, the system comprising: an imaging system; and the injector system of any of clauses 1-13, wherein the injector system is in communication with the imaging system.

DETAILED DESCRIPTION

For purposes of the description hereinafter, spatial orientation terms shall relate to the embodiment as it is oriented in the drawing figures. However, it is to be understood that the various embodiments of this disclosure may assume alternative variations and step sequences, except where expressly specified to the contrary. It is also to be understood that the specific devices and processes illustrated in the attached drawings, and described in the following specification, are simply exemplary. Hence, specific dimensions and other physical characteristics related to the embodiments disclosed herein are not to be considered as limiting.

As used in the specification, the singular form of "a", "an", and "the" include plural referents unless the context deafly dictates otherwise.

Unless otherwise indicated, all ranges or ratios disclosed herein are to be understood to encompass any and all subranges or sub-ratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

All documents, such as but not limited to issued patents and patent applications, referred to herein, and unless otherwise indicated, are to be considered to be "incorporated by reference" in their entirety.

As used herein with respect to an injection procedure, the term "protocol" refers to a group of parameters such as flow rate, flow volume, flow duration, etc. that define the amount of fluid(s), such as a contrast agent or a flush fluid; to be delivered to a patient during a fluid delivery procedure. Such parameters can change over the course of the procedure.

The protocols that are the subject of this disclosure, which may be referred to herein as "split bolus protocols," define the amount of fluid to be delivered during a split bolus injection procedure. The split bolus protocols employ a split bolus technique in which the delivery of a contrast agent is split into multiple (e.g., two, three, or four) discrete contrast injections, each of which includes at least the delivery of a contrast bolus, and may also include, for example, an amount of a flush fluid or diluent. The contrast injections may be separated from each other by a pause or delay period wherein no fluid delivery is occurring, or at least no contrast agent is being delivered. The pause period may be of variable duration or it may be of a consistent duration. For example, the delay between each injection may be the same or it may vary.

Split bolus protocols according to this disclosure may; for example, include t three, four, or more discrete contrast injections. The final such contrast injection, which may be referred to as the "diagnostic injection," can provide a contrast bolus used for arterial phase enhancement, or first pass imaging. One or more of the contrast injections that precede the diagnostic injection may be referred to herein as the "loading injections." The loading injections may provide a bolus or boluses of contrast sufficient to ensure the contrast is properly loaded into the patient. Split bolus protocols according to this disclosure may also include a test injection that occurs before the contrast injections referenced above. The test injection which may be used, for example, to test for catheter placement, is optional and, for purposes of this disclosure, is not considered to be one of the "contrast injections" of the split bolus protocol.

By way of example, a split bolus protocol according to the present disclosure can include two loading injections and one diagnostic injection for a total of three discrete contrast injections. A first loading injection can provide a first loading bolus that primarily serves to load the body tissues or the kidneys, ureter, and/or bladder of the patient with contrast agent. The parameters of this first loading injection, including the volume of contrast, the contrast flow rate, and the length of the pause period that follows the first loading injection, can be selected to permit the contrast agent delivered through this injection to absorb out of the blood stream and diffuse into tissues for parenchymal imaging or, depending on the length of the delay, to be processed and collected in the excretory system. A second loading injection can provide a second loading bolus that primarily focuses on the venous system. For example, the parameters of the second loading injection can be selected to create a near-uniform distribution of contrast agent in the blood pool where both the venous and arterial sides have equal amounts of contrast agent. The pause period that follows this second loading injection can be sufficient to allow the contrast agent to recirculate through the path of veins→heart→lungs-→heart→arteries multiple times but not be so long that a significant amount of the contrast agent leaves the blood pool. A goal of this second loading injection can be to enable the imaging of the entire vascular system during the subsequent scan acquisition (following the diagnostic injection) where the arterial structures are of interest. This technique may show particular utility in urography and trauma imaging. A diagnostic injection, which can follow the second loading injection, can provide a diagnostic bolus that primarily serves to bring the enhancement levels of the body regions of interest up to a threshold value so that the scanner acquisition that follows the diagnostic injection is effective.

Each contrast injection (e.g., each loading injection and diagnostic injection) may include more than one phase, such as two phases, where, in a first phase, a contrast bolus is delivered and, in a second phase, a flush fluid, such as saline, is delivered. In general, the second phase immediately follows the first phase. Administration of a flush fluid immediately following delivery of a contrast bolus serves several purposes, as is known in the art, including helping flush or push the contrast bolus through the patient and helping clear the catheter lines of residual contrast agent. For example, a loading injection can include a first phase in which an amount of contrast agent is injected at a set flow rate for a set duration and, immediately upon the completion of the injection of contrast agent, a second phase in which an amount of saline is injected at a set flow rate for a set duration. In some non-limiting embodiments, the loading injection is deemed to be complete upon the conclusion of the saline phase, and a pause period occurs before, for example, the next loading injection or a diagnostic injection. For example, after a loading injection is complete, there can be a pause, followed by a first phase of a diagnostic injection during which an amount of contrast agent at a set flow rate for a set duration is injected, which is then immediately followed by a second phase of the diagnostic injection in which an amount of saline is injected at a set flow rate for a set duration.

Figure 1:
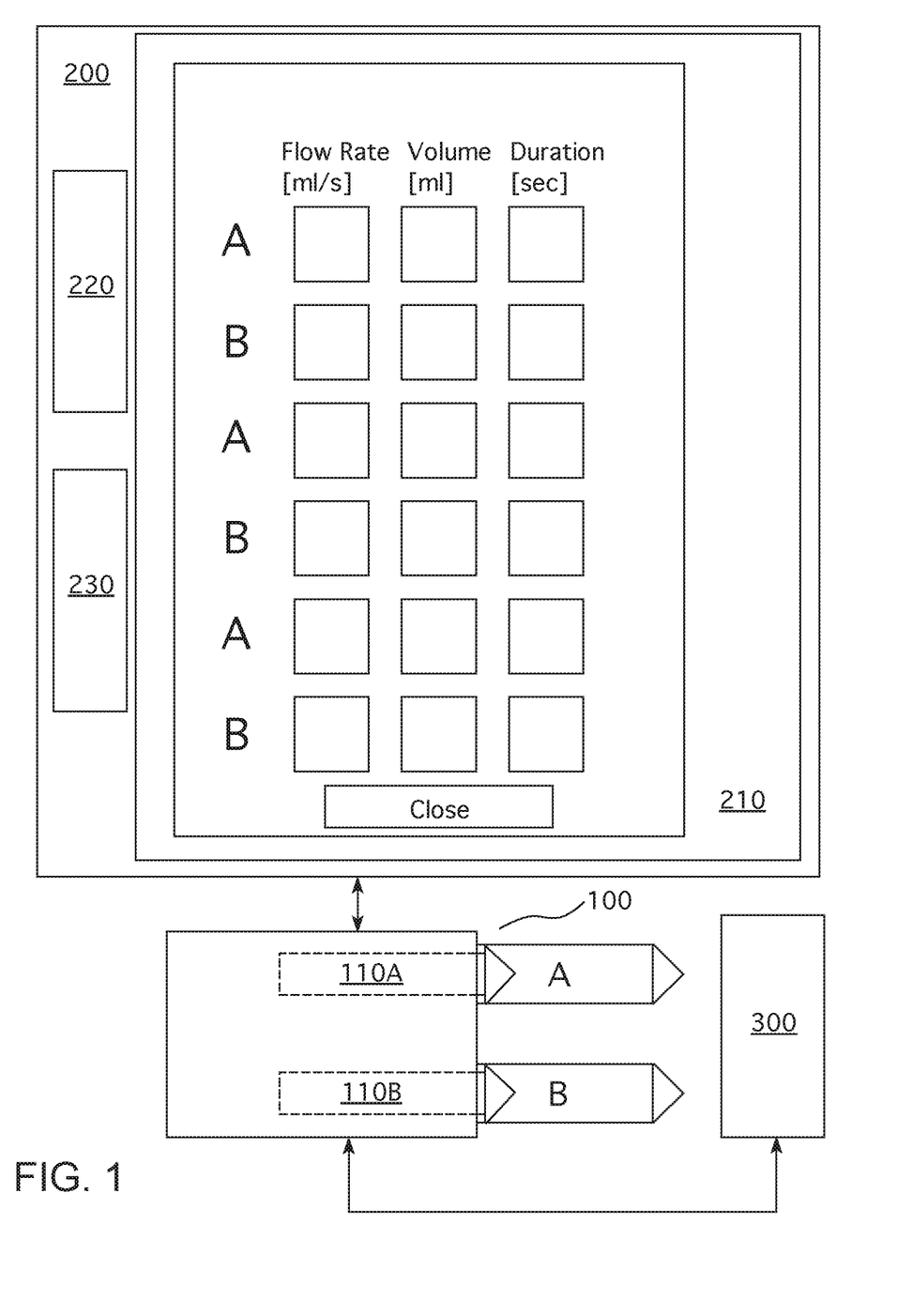
FIG. 1 illustrates an embodiment of a multi-phasic graphical user interface (GUI) of the type used in a two-syringe injector system, also shown in FIG. 1, to set forth parameters for an injection protocol comprising a plurality of phases.

In several embodiments of the present disclosure, an injector system, such as a dual syringe injector system 100 as illustrated in FIG. 1 and as, for example, disclosed in U.S. Pat. Nos. 6,643,537 and 7,553,294, both of which are incorporated herein by reference is used. The injector system 100 can include two fluid delivery sources, sometimes referred to as source "A" and source "B" herein, which may be in the form of syringes that are operable to introduce a first fluid and/or a second fluid to the patient independently. In some non-limiting embodiments, the first fluid may be a contrast agent and the second fluid may be a flush fluid such as saline. The first and/or second fluids may be delivered, for example, simultaneously, simultaneously in different volumetric flow proportion to each other, or sequentially or subsequent to each other (that is, A then B, or B then A).

In the embodiment of FIG. 1, source A is in operative connection with a pressurizing mechanism such as a drive member 110A, and source B is in operative connection with a pressurizing mechanism such as a drive member 110B. The injector system includes a controller 200 in operative connection with injector system 100 that is operable to control the operation of drive members 110A and 110B to control injection of fluid A (for example, contrast agent) from source A and injection of fluid B (for example, saline) from source B, respectively. Injector system can, for example, have associated with it a display 210 on which a graphical user interface (GUI) is displayed. Controller 200 can also include a processor 220 (for example, a digital microprocessor as known in the art) in operative connection with a memory 230.

Figure 2:
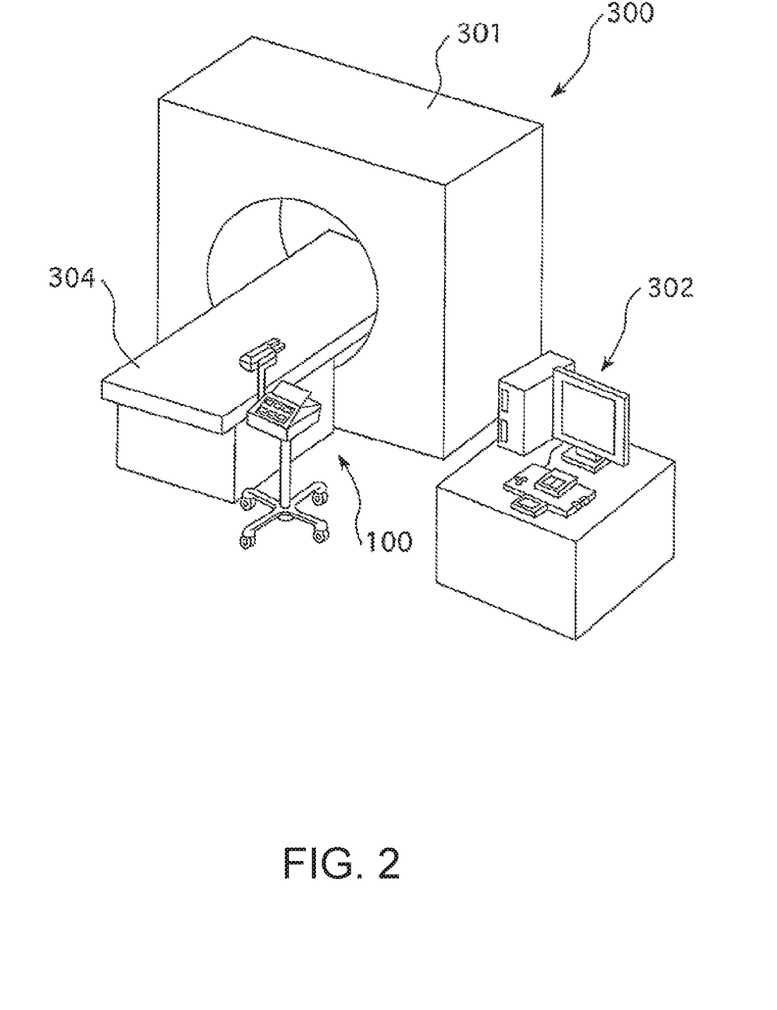
FIG. 2 illustrates a patient imaging environment according to one non-limiting embodiment of the present invention.

In some non-limiting embodiments of the disclosure, an imaging system 300, as illustrated in FIG. 2, can also be used. Imaging system 300 can, for example, be a CT system, a Magnetic Resonance Imaging (MRI) system, an ultrasound imaging system, a Positron Emission Tomography (PET) system or another imaging system. Imaging system 300 can include an imager 301 that is commonly moved with respect to the patient bed 304. One example of an imaging system 300 is a CT system, which includes a CT scanner used to bombard a subject with X-rays from an X-ray source. The X-rays emitted from X-ray source pass through tissues, organs, and structures of the subject at different rates (some of which is absorbed by such tissues, organs, and structures) depending on the density and type of matter which the X-rays pass through, including the presence (or absence) of a contrast agent in the tissue and/or organs. Sensors disposed within a ring detect the amount of radiation that passes through the subject. The injector system 100 and/or an input device 302, such as a computer, (which may include display 210) can be in communicative connection with imaging system 300 so as to transmit signals therebetween and one, a plurality, or all the components of the injector system 100, input device 302, and imaging system 300 can be integrated. Communication between the injector system 100, the input device 302, and the imaging system 300 can be through a wired or wireless network connection, such as an Intranet, LAN, WAN, or an Internet connection.

In one non-limiting embodiment, injector system 100 transmits a timing signal to imaging system 300 indicating that one or more injections have been completed. Imaging system 300 can use this timing signal to determine the appropriate time to begin an image acquisition scan. In some non-limiting embodiments according to the present disclosure in which a split bolus technique is used, a timing signal may be transmitted from injector system 100 to imaging system 300 only after completion of the diagnostic injection while no such timing signals are transmitted following any of the other injections of the split bolus protocol, including the loading injections.

In some non-limiting embodiments of the present disclosure, the parameters for a split bolus protocol, such as the parameters of one or more of the contrast injections of a split bolus protocol, are determined by a parameter generation system. The parameter generation system may be integrated with the injector system 100 and/or imaging system 300, or it may be part of one or more separate systems that are in communication with the injector system 100 and/or imaging system 300, such as by way of the communication means discussed above. The parameter generation system may be software in the form of programming instructions, or an algorithm, residing in non-transitory computer readable storage media that resides on, or is accessible by, the injector system 100 and/or imaging system 300. When executed by a processor, the programming instructions can enable the injector system 100 and/or imaging system 300 to operate as a parameter generation system and perform the operations described herein. The parameter generation system may determine the parameters of a split bolus protocol according to the present disclosure based on certain information, including, for example, contrast agent concentration (for example, iodine concentration in the case of a CT procedure), patient data (for example, body weight, body regions or compartments of interest, body mass index, body surface area, height, gender, age, cardiac output, etc.), the type of scan being performed, the type of catheter inserted into the patient for intravascular access, the number of injections into which the contrast injection is to be split for purposes of applying the split bolus technique described above, and the length of any pause period that may occur between the contrast injections.

For example, the split bolus protocol can include parameters (e.g., contrast agent flow rate, injection duration, and/or volume of contrast agent) for each of the multiple contrast injections (e.g., loading boluses, diagnostic bolus) that together constitute a split bolus injection procedure. The parameter generation system can, according to the present disclosure, be configured to calculate the parameters for each of the contrast injections of the split bolus protocol in a one-pass calculation based on the configuration and input values. For example, the parameter generation system can determine the injection parameters, including the injection volumes, the injection flow rates, the injection durations, and the pause between injections, for a split bolus injection procedure that includes one or more, such as two, loading injections and one or more, such as one, diagnostic injections through a one-pass calculation.

It has been recognized that different patients have different dosing requirements. For example, U.S. Pat. Nos. 5,840,026 and 6,385,483, assigned to the assignee of the present disclosure, the disclosures of which are incorporated herein by reference, disclose devices and methods to customize the injection to the patient using patient specific data derived before or during an injection. Likewise, U.S. Pat. No. 8,295,914, assigned to the assignee of the present disclosure, the content of which is incorporated herein by reference, also discloses customization of injections to a patient using patient specific data and sets forth a number of models to describe a time enhancement output for a given input or protocol. In addition, U.S. Pat. No. 9,302,044, assigned to the assignee of the present disclosure, the content of which is incorporated herein by reference, discloses a patient-based parameter generator system for medical injection protocols. The techniques discussed in each of these referenced documents can be useful in the present disclosure in determining, for example, the amount of contrast agent and/or the amount of flush fluid that should be injected during a split bolus injection procedure. However, it should be noted that these disclosures do not apply the techniques discussed therein in connection with a split bolus protocol.

Because optimal sets of flow rates, volumes, and pause durations between contrast injections in a split bolus protocol are not readily known to the operator of the injector when utilizing a split bolus technique, the present disclosure eases the task of an operator by providing a split bolus protocol effective for the type of procedure being performed. Such protocols can be established using information as discussed above, such as information about the injection itself, such as the concentration of iodine and/or the catheter gauge, information about the patient, such as the patient weight, height, body mass index, or sex, information about the scanner, such as the tube voltage to be used, and other information that may be available. This information can be received from, for example, the Hospital Information System (HIS), the Radiology Information System (RIS), or another information source within or available to the imaging facility. This information may also be entered by an operator through an input device, such as an input device 302 associated with the injector system 100, imaging system 300, and/or the parameter generation system.

As part of this process of determining the parameters of a split bolus protocol, the operator can, for example, choose the concentration of contrast agent (for example, concentration of iodine in a CT procedure) to be delivered into a patient. This choice can be made, for example, by a selection mechanism, such as a drop down menu or other means providing available options to an operator on a graphical user interface. This choice may also be made by direct input of numerical values on a graphical user interface or using a keyboard, mouse, or other input mechanism, including ones that may be associated with input device 302. The concentration value may also be transmitted to the parameter generation system from another system, such as HIS or RIS. The clinical operator can also select the gauge of the catheter inserted into that specific patient. Catheter size can be entered so that in subsequent steps, when the volumetric flow rate is determined, the pressure head to be developed in a disposable fluid path set can be calculated (for example, via a computer program). Alternatively, one or more sensors can be provided to sense catheter size and provide this information to the injector system.

The operator can also, for example, be prompted to enter an indication of the number and type of contrast injections to be included in the split bolus injection procedure. For example, the procedure may include two loading boluses and a diagnostic bolus. This information, as well as the other information referenced herein, can be received through, for example, an input to an input device 302 associated with the injector system 100, imaging system 300, and/or the parameter generation system, such as in the form of a direct text entry or a selection from a drop down menu or other mechanism, or from another source, such as those discussed above (e.g., HIS, RN). If the procedure includes a test injection, the parameter generation system may receive a value of the volume (e.g., ml) and duration (e.g., sec) of the test injection, from which the parameter generation system can determine the flow rate of the test injection (ml/sec).

The operator can, for example, also be prompted to enter values for other variables (for example, patient physiological variables such as the patient's weight, height, body mass index, gender, etc.). An example of an embodiment or implementation of this is to provide a keypad on the user interface into which the operator enters the patient's weight in pounds or kilograms. In another embodiment, the operator chooses a weight range from among low, mid and high ranges. Such variables can also be measured by one or more sensing devices associated with the system and/or read electronically or digitally from patient records as may be kept in a hospital database.

A variable weighting factor (mg contrast/Body weight kg) can be used to determine the dose of contrast (e.g., dose of Iodine) for the patient in each of the several contrast injections of the split bolus injection procedure (e.g., the dose of contrast in each loading injection and the dose of contrast in the diagnostic injection). These weighting factors can vary depending on the type and purpose of the injection. For example, the weighting factor for a loading bolus may be different than the weighting factor for a diagnosis bolus. The weighting factors for a first loading bolus may also vary from the weighting factors of a second loading bolus. Alternatively, the weighting factors for each of the contrast injections may be the same. In some non-limiting embodiments, the weighting factors may be determined at the time of configuration by running simulations, such as a large number of simulations, of the enhancement levels reached in the body regions of interest for a range of patient habitus (e.g., sizes) and applying an optimization, such as a heuristic optimization, to determine what fraction, and total amount, of the contrast agent should be delivered in each of the several contrast injections of the split bolus injection procedure, as well as to determine the scan timing.

The parameter generation system of the present invention may also receive one or more boundary conditions, an example of which is a flow rate limit, which indicates the maximum flow rate a patient should be subjected to. These boundary conditions can be stored by the parameter generation system and act as checks to ensure that any calculated and/or entered values do not exceed the recommended limits for a particular patient and/or procedure. In several embodiments, published results of previous studies can be used to provide the boundary conditions for the dosing scale of the present disclosure.

The parameter generation system may also receive a desired duration of one or more of the contrast injections (e.g., length, in sec., of each injection). The desired duration of each contrast injection can be used along with patient weight and the above-described weighting factor to determine the contrast delivery rate for that particular contrast injection, which may be expressed in terms of volume of contrast per unit of time (e.g., mgI/sec). From the contrast delivery rate (e.g., mgI/sec) and information about the contrast concentration (e.g., mgI/ml), the parameter generation system can determine the flow rate (e.g., ml/sec) of contrast to use for one or more of the contrast injections. For example, using the patient weight, the parameter generation system can determine the appropriate weighting factor for each loading injection and diagnostic injection, such as by reference to a lookup table that contains the weighting factors for each contrast injection as a function of weight. From that weighting factor, the contrast concentration, and the desired duration of each injection, the parameter generation system can determine the flow rate (e.g., ml/sec) sufficient to deliver the appropriate volume of contrast in each of the contrast injections (e.g., for each loading injection and diagnostic injection). This calculated flow rate can be compared to the boundary conditions to ensure that the boundary conditions are not exceeded. Alternatively, the parameter generation system can receive a desired flow rate value and, from this information along with the patient weight and weighting factor, determine the injection duration for each contrast injection. By way of further example, the volume of the contrast agent that is to be injected during each contrast injection can be calculated using the formula: V=weight*X*Y, wherein Y is a function of the concentration of the contrast agent, X is a weighting factor that may differ between the loading injection and the diagnostic injection, and V is the volume of contrast agent.

To the extent any of the contrast injections have, in addition to a contrast phase, a flush phase, the parameter generation system can also receive information about the flush volume, flush duration, and/or flush flow rate. For example, the parameter generation system can receive, for each contrast injection, the total amount of the flush fluid and the flow rate of the flush fluid. The parameter generation system can use this information to develop the protocol parameters for the second phase of one or more of the contrast injections of the split bolus injection procedure. In one non-limiting embodiment, the flush fluid, flush volume, and flush flow rate can be identical for each contrast injection, and in this embodiment the parameter generation system need only receive one set of flush parameters which can then be applied to each contrast injection. In another non-limiting embodiment, the flush volume can vary between the contrast injections while the flush flow rate remains the same. For example, the loading bolus(s) may have a larger flush volume than the diagnostic bolus or the diagnostic bolus may have a larger flush volume than the loading bolus.

The parameter generation system may also receive a value of the pause, or delay, period between consecutive contrast injections. For example, the parameter generation system may receive, as an input from an operator, a value, in seconds, for the length of the pause between the end of a first loading injection and the beginning of a second loading injection and/or between the end of the first or second loading injection and the beginning of the diagnostic injection. If no such value is provided, the parameter generation system may apply a default value, such as 90 seconds. In addition, in some non-limiting embodiments, the parameter generation system may be configured to include a start duration threshold, which may be a maximum value for the pause between contrast injections. This start duration threshold may be, for example, 90 seconds, and may protect against situations in which an operator fails to specify a value of the pause or inadvertently specifies a value that is unreasonably long. For example, in the event the entered pause value exceeds the start duration threshold, the injector system 100 may override the entered pause value and automatically start the next injection at the conclusion of the start duration threshold.

In some non-limiting embodiments, one or more of the contrast injections may be initiated manually by an operator of the injector system 100. In such an event, an operator can be prompted with one or more reminders that the time to initiate a contrast injection is approaching. For example, a visual and/or auditory message may issue indicating that a loading or diagnostic contrast injection should be initiated in, for instance, 10 seconds, in 5 seconds, in 1 second, or immediately. The operator may be prompted to specify text displayed for each reminder as well as a name for the reminder, or the system may chose default text and/or name. The prompt can appear on a display, such as a display associated with an input device 302.

Figure 3:
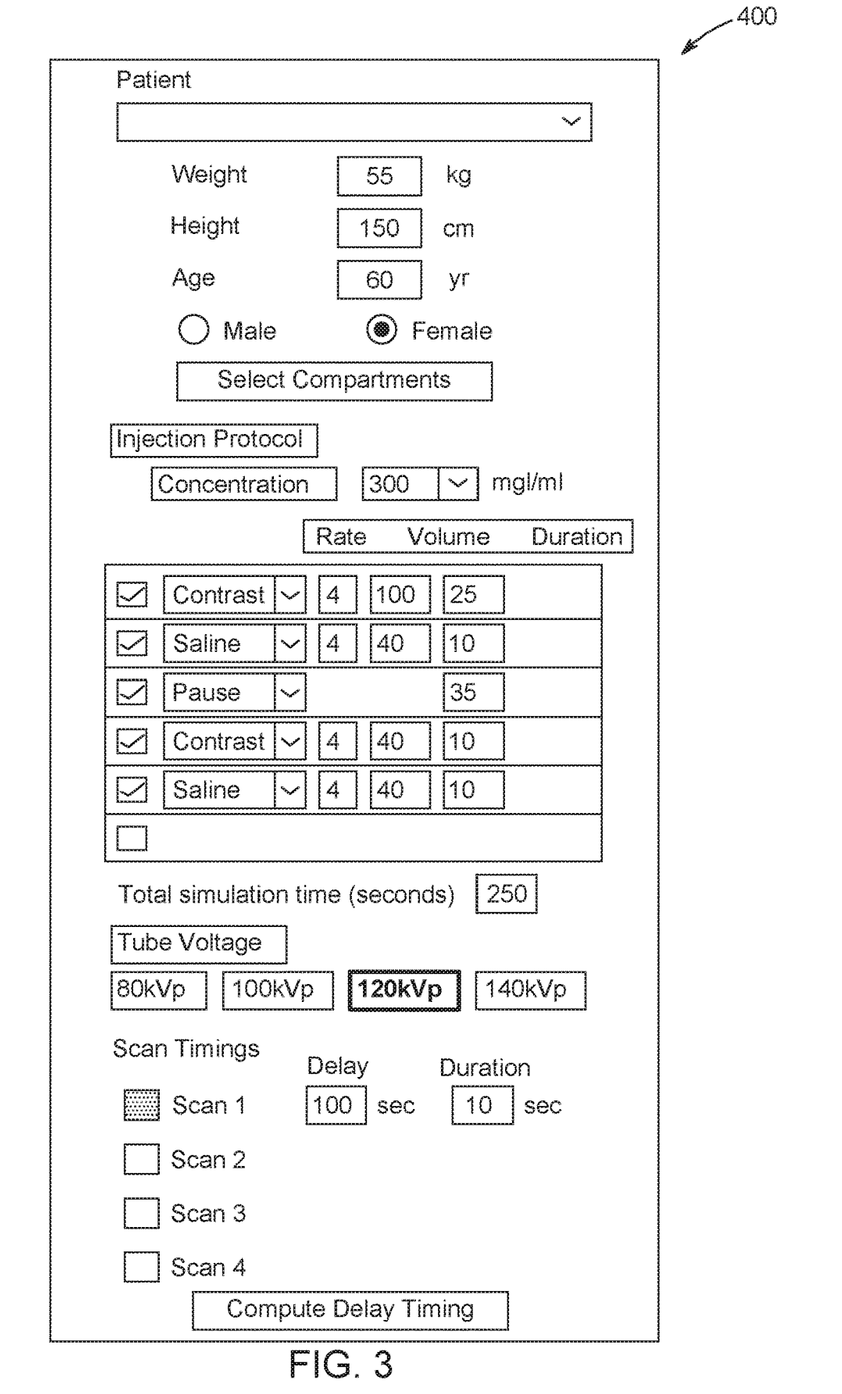
FIG. 3 illustrates a graphical user interface according to one non-limiting embodiment of the present invention.

Once the split bolus protocol is determined, the parameter generation system may populate certain parameters thereof on a graphical user interface associated with an input device 302. FIG. 3 provides an example graphical user interface 400 that has been populated with details of a split bolus protocol. This graphical user interface 400 may also be used to input information to input device 302.

As shown in FIG. 3, the weight, age, height, and sex of the patient are known and populated in the appropriate area of the graphical user interface 400. This information may have been manually entered or populated using one or more data sources, as described above. Alternatively, graphical user interface 400 can include a drop down menu from which an operator can select a patient by, for example, name or patient ID, and, upon making such selection, the weight, age, height, and sex can be populated from information about the selected patient stored in a database. FIG. 3 also displays information on the concentration of the contrast agent, expressed in terms of mgI/ml. In this embodiment, the concentration is entered directly into graphical user interface 400 by the operator using a drop down menu. FIG. 3 also displays the contrast injection parameters of the split bolus protocol in terms of flow rate (in ml/sec) and volume (in ml). This exemplary split bolus protocol includes a first contrast injection having a first phase in which 100 ml of contrast is injected at a rate of 4 ml/sec for a total duration of 25 sec followed by second phase in which 40 ml of saline is injected at a rate of 4 ml/sec for a total duration of 10 sec. The procedure also includes a pause of 35 sec before beginning the second contrast injection. The second contrast injection has a first phase in which 40 ml of contrast is injected at a rate of 4 ml/sec for a total duration of 10 sec followed by second phase in which 40 ml of saline is injected at a rate of 4 ml/sec for a total duration of 10 sec. As shown in FIG. 3, in this embodiment, the tube voltage of the scanner is set at 120 kVp, though other options for the tube voltage are also available.

In addition, in the embodiment shown in FIG. 3, the scan timing is set at a delay of 100 sec and the scan duration is set for 10 sec. The scan delay in this embodiment is the time from the initiation of the contrast injection procedure (i.e., before the first phase of the first contrast injection begins) to the start of the scanning procedure. The length of the scan delay is typically selected to allow sufficient time for the contrast to propagate through the body and be absorbed by the areas of interest, as would be understood by a person skilled in the art upon reading the present disclosure.

Figure 4:
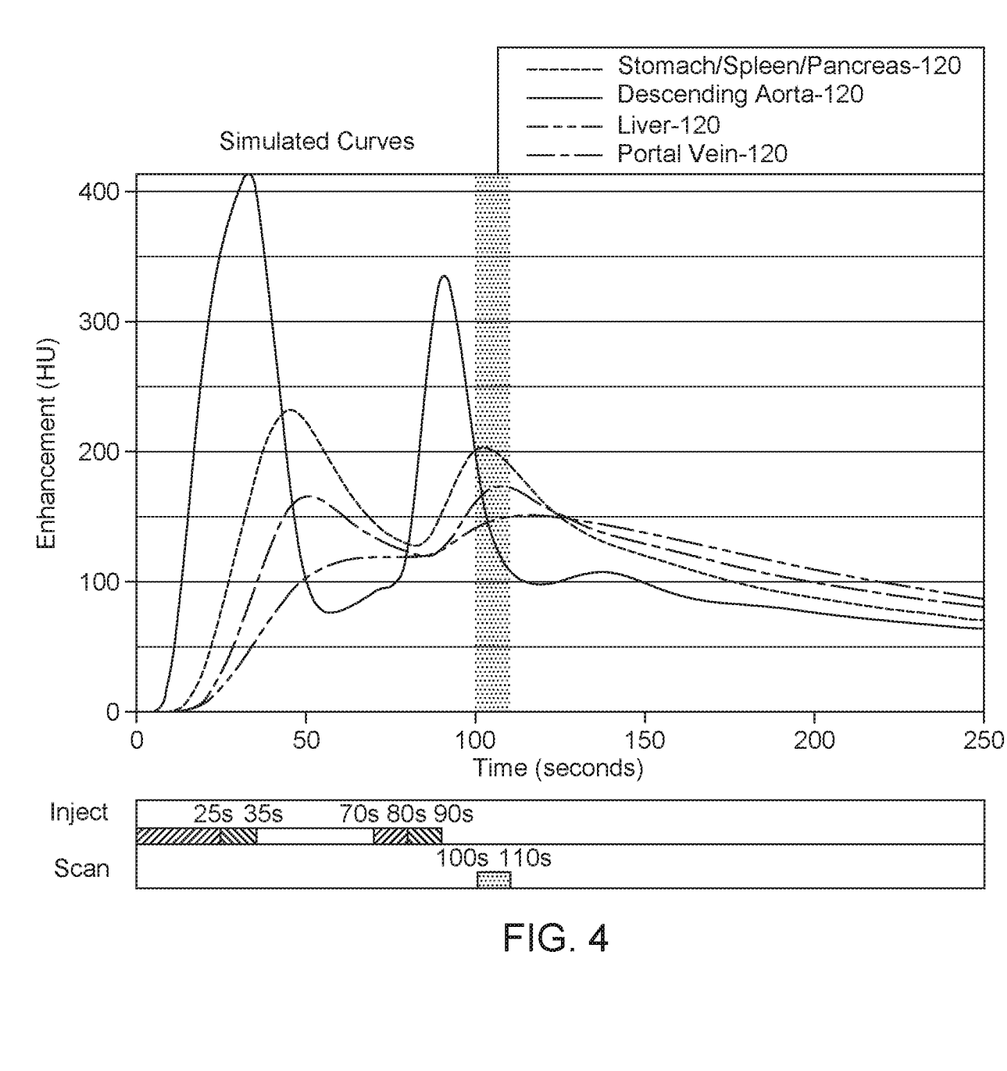
FIG. 4 illustrates a set of simulated enhancement curves according to one non-limiting embodiment of the present invention.

FIG. 4 represents a set of simulated enhancement curves generated through the split bolus injection protocol illustrated in FIG. 3. The curves in FIG. 4 track the enhancement in various areas of interest (e.g., stomach/spleen/pancreas, descending aorta, liver, and portal vein) as a function of time relative to the timing of the contrast injections. Also provided in FIG. 4 is a timeline of the contrast injections and scan window. As seen in FIG. 4, applying the split bolus protocol of FIG. 3 provides multiple enhancement peaks in each of the areas of interest. The first contrast injection (e.g., 100 ml at a flow rate of 4 ml/sec) serves as a loading bolus to load the contrast into the patient. The second contrast injection (e.g., 40 ml at a flow rate of 4 ml/sec) acts as a diagnostic bolus and further increases the enhancement from the loading level to a level effective for arterial phase enhancement. The scan window is selected to coincide with a point in time when the enhancement values in multiple regions of interest are simultaneously above a threshold level, which in this case is 150 HU. By using a split bolus technique, a single scan timed to coincide with the simultaneous enhancement period (e.g., 100-110 sec) allows an operator to simultaneously capture a diagnostic image of several areas of interest through a single scan.

Figure 5:
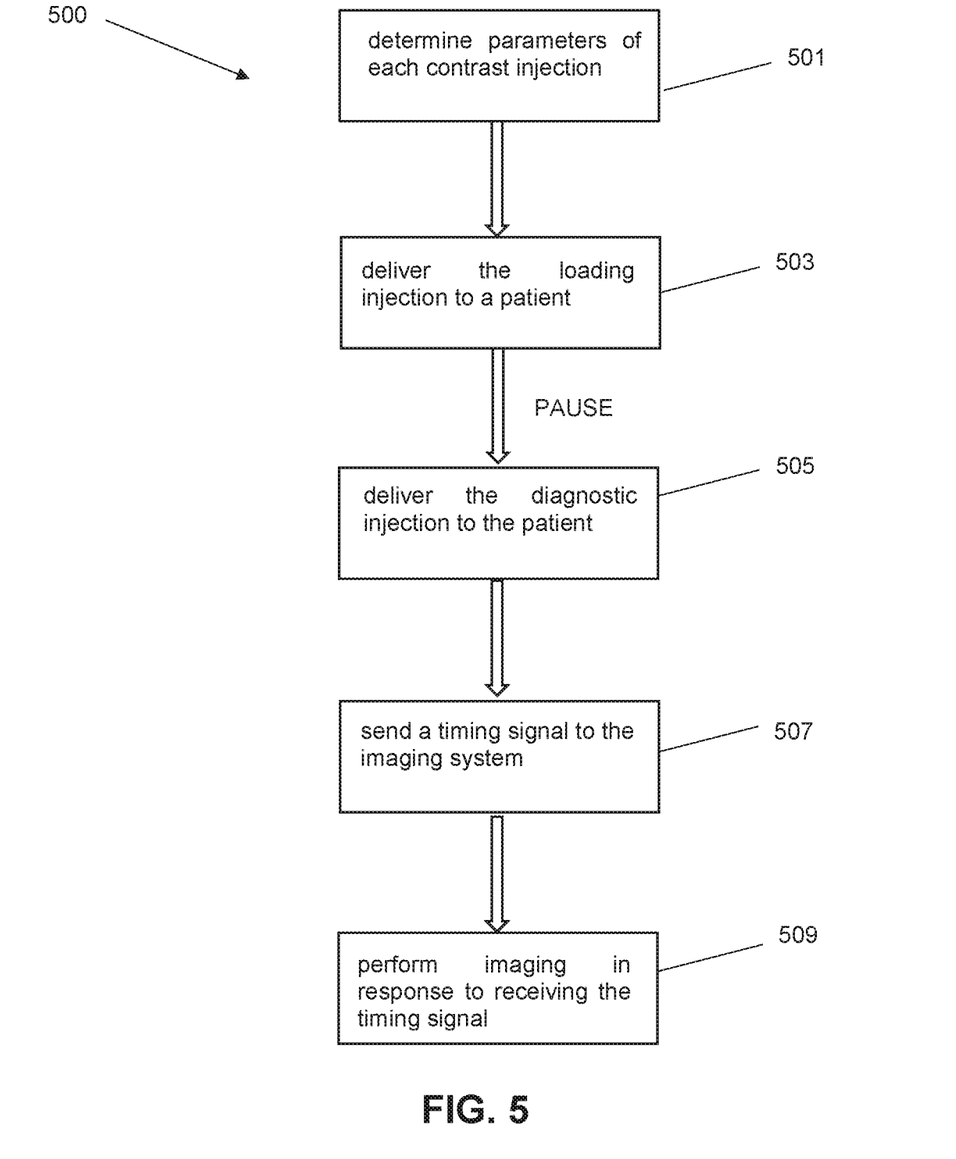
FIG. 5 is a flowchart of a non-limiting embodiment of a method for method for patient imaging using a split bolus injection technique.

Referring to FIG. 5, FIG. 5 is a flowchart of a non-limiting embodiment of a method 500 for patient imaging using a split bolus injection technique. The method can include a step 501 of determining parameters of a loading injection and a diagnostic injection. This step 501 can be performed by a parameter generation system, as discussed above. The method can also include a step 503 of performing the loading injection so as to deliver the contrast agent and/or flush fluid associated with the loading injection to the patient according to the parameters determined in step 501. Step 503 can be performed by injector system 100. As described above, a pause period can follow step 503 and precede the next step 505, which involves delivering the contrast agent and/or flush fluid associated with the diagnostic injection to the patient according to the parameters determined in step 501. Step 505 can also be performed by injector system 100. After step 505 is complete, injector system 100 can perform step 507, which involves sending a timing signal to imaging system 300 indicating that the diagnostic injection has been completed. In step 509, the imaging system 300 can perform an imaging procedure of the patient in response to receiving the timing signal.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:

1. An injector system for injecting a contrast agent into a patient in connection with a contrast enhanced imaging procedure to be performed on the patient using an imaging system, the injector system comprising:
   a processor; and
   a non-transitory storage medium having programming instructions stored therein that, when executed by the processor, enable the injector system to operate as a parameter generation system for use in determining parameters associated with a split bolus injection protocol via which injection of the contrast agent by the injector system is controlled,
   wherein the split bolus injection protocol includes at least a loading injection and a diagnostic injection, wherein the loading injection is performed before the diagnostic injection, and wherein a pause separates the loading injection from the diagnostic injection, and
   wherein the injector system is configured to perform the loading injection and the diagnostic injection according to the parameters determined by the parameter generation system.

2. The injector system of claim 1, wherein the parameter generation system determines one or more of a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

3. The injector system of claim 2, wherein the parameter generation system determines the volume of the contrast agent to be injected during the loading injection, the flow rate of the contrast agent to be injected during the loading injection, the volume of the contrast agent to be injected during the diagnostic injection, and the flow rate of the contrast agent to be injected during the diagnostic injection.

4. The injector system of claim 1, wherein the split bolus injection protocol includes a second loading injection, and the parameter generation system determines at least one of a volume of the contrast agent to be injected during the second loading injection and a flow rate of the contrast agent to be injected during the second loading injection.

5. The injector system of claim 2, wherein the split bolus injection protocol includes a second loading injection, and the parameter generation system determines at least one of a volume of the contrast agent to be injected during the second loading injection and a flow rate of the contrast agent to be injected during the second loading injection.

6. The injector system of claim 1, further comprising a graphical user interface configured to display the parameters determined by the parameter generation system
   wherein the graphical user interface is configured to display a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

7. The injector system of claim 1, wherein the parameter generation system determines a volume of the contrast agent that is to be injected during the loading injection and a volume of the contrast agent that is to be injected during the diagnostic injection at least partly on the basis of a concentration of the contrast agent and at least partly on the basis of a function X having a value that differs depending upon a weight of a patient.

8. The injector system of claim 7, further comprising an input device for entering into the parameter generation system the concentration of the contrast agent and the weight of the patient.

9. The injector system of claim 7, wherein the volume of the contrast agent that is to be injected during the loading injection and the volume of the contrast agent that is to be injected during the diagnostic injection are each independently calculated using the formula: $V = \text{weight} \cdot X \cdot Y$, wherein Y is a function of the concentration of the contrast agent, and wherein X may differ between the loading injection and the diagnostic injection.

10. The injector system of claim 9, wherein X is determined for the weight of a particular patient from at least one of:
    an algorithm in which X is calculated as a function of weight; and
    a table wherein X is set forth as a function of weight.

11. The injector system of claim 1, wherein the injector system is configured to send a timing signal to the imaging system after the diagnostic injection.

12. A method for patient imaging using a split bolus injection technique, the method comprising:
    determining, by a parameter generation system, parameters of a loading injection and a diagnostic injection, wherein each of the loading injection and the diagnostic injection comprise a volume of a contrast agent;
    performing, by an injector system, the loading injection so as to deliver the loading injection to a patient;
    performing, by the injector system, the diagnostic injection so as to deliver the diagnostic injection to the patient, wherein a pause of a predetermined period of time occurs between the loading injection and the diagnostic injection;
    sending, from the injector system to an imaging system, a timing signal indicating that the diagnostic injection has been completed; and performing, by the imaging system, an imaging procedure of the patient in response to receiving the timing signal.

13. The method of claim 12, wherein the parameter generation system determines one or more of a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

14. The method of claim 13, wherein the parameter generation system determines the volume of the contrast agent to be injected during the loading injection, the flow rate of the contrast agent to be injected during the loading injection, the volume of the contrast agent to be injected during the diagnostic injection, and the flow rate of the contrast agent to be injected during the diagnostic injection.

15. The method of claim 12, further comprising:
determining, by the parameter generation system, parameters of at least one of a volume of the contrast agent to be injected during a second loading injection and a flow rate of the contrast agent to be injected during the second loading injection.

16. The method of claim 12, further comprising:
displaying, on a graphical user interface, the parameters determined by the parameter generation system
wherein the graphical user interface displays a volume of the contrast agent to be injected during the loading injection, a flow rate of the contrast agent to be injected during the loading injection, a volume of the contrast agent to be injected during the diagnostic injection, and a flow rate of the contrast agent to be injected during the diagnostic injection.

17. The method of claim 12, wherein the parameter generation system determines a volume of the contrast agent that is to be injected during the loading injection and a volume of the contrast agent that is to be injected during the diagnostic injection at least partly on the basis of a concentration of the contrast agent and at least partly on the basis of a function X having a value that differs depending upon a weight of a patient.

18. The method of claim 17, wherein the volume of the contrast agent that is to be injected during the loading injection and the volume of the contrast agent that is to be injected during the diagnostic injection are each independently calculated using the formula: $V=\text{weight}*X*Y$, wherein Y is a function of the concentration of the contrast agent, and wherein X may differ between the loading injection and the diagnostic injection.

19. The method of claim 18 wherein X is determined for the weight of a particular patient from at least one of:
an algorithm in which X is calculated as a function of weight; and
a table wherein X is set forth as a function of weight.

20. A system for patient imaging, the system comprising:
an imaging system; and
the injector system of any of claims 10 and 11, wherein the injector system is in communication with the imaging system.

* * * * *

UNITED STATES PATENT AND TRADEMARK OFFICE
CERTIFICATE OF CORRECTION

PATENT NO. : 11,565,035 B2
APPLICATION NO. : 16/619515
DATED : January 31, 2023
INVENTOR(S) : Volkar et al.

It is certified that error appears in the above-identified patent and that said Letters Patent is hereby corrected as shown below:

In the Claims

In Column 16, Line 27, in Claim 20, delete "claims 10 and 11," and insert -- claims 1-11, --, therefor.

Signed and Sealed this
Twenty-seventh Day of June, 2023

Katherine Kelly Vidal
*Director of the United States Patent and Trademark Office*